(12) United States Patent
Waller (10) Patent No.: US 11,331,513 B2
(45) Date of Patent: May 17, 2022

(54) PAIN TREATMENT DEVICE

(71) Applicant: National Laser Company, Salt Lake City, UT (US)

(72) Inventor: Kevin Waller, Sandy, UT (US)

(73) Assignee: National Laser Company, Salt Lake City, UT (US)

( * ) Notice: Subject to any disclaimer, the term of this patent is extended or adjusted under 35 U.S.C. 154(b) by 226 days.

(21) Appl. No.: 16/563,861

(22) Filed: Sep. 7, 2019

(65) Prior Publication Data

US 2021/0069523 A1 Mar. 11, 2021

(51) Int. Cl.
*A61N 5/06* (2006.01)
*A61N 5/067* (2006.01)

(52) U.S. Cl.
CPC ............ *A61N 5/0613* (2013.01); *A61N 5/067* (2021.08); *A61N 2005/0632* (2013.01); *A61N 2005/0644* (2013.01); *A61N 2005/0659* (2013.01); *A61N 2005/0662* (2013.01)

(58) Field of Classification Search
CPC ................ A61N 5/0613; A61N 5/0616; A61N 2005/0644; A61N 2005/0632
USPC ........................................ 607/88–91; 606/9
See application file for complete search history.

(56) References Cited

U.S. PATENT DOCUMENTS

| 6,221,095 B1 | 4/2001 | Van Zuylen et al. |
| 8,771,326 B2 | 7/2014 | Myeong et al. |
| 9,597,526 B2 | 3/2017 | Hacco et al. |
| 2007/0276359 A1* | 11/2007 | Segal ...................... A61N 5/06 606/11 |
| 2008/0103563 A1 | 5/2008 | Powell et al. |
| 2010/0076529 A1* | 3/2010 | Tucker ................. A61N 5/0617 607/90 |
| 2010/0121419 A1 | 5/2010 | Douglas |
| 2011/0015707 A1* | 1/2011 | Tucker ................. A61N 5/0616 607/90 |
| 2011/0106222 A1 | 5/2011 | Wilson et al. |

(Continued)

FOREIGN PATENT DOCUMENTS

| KR | 101427842 A | 2/2014 |
| KR | 101581665 B1 | 12/2015 |

(Continued)

OTHER PUBLICATIONS

MedTek LED, Rejuv, POLY, "How Does Red Light Set Back the Clock?", dated May 31, 2019, pp. 1-13.

*Primary Examiner* — John R Downey
(74) *Attorney, Agent, or Firm* — Kunzler Bean & Adamson; Bruce R. Needham (57) ABSTRACT

An apparatus for pain treatment includes first and second treatment heads, where each treatment head includes one or more light sources with different wavelengths oriented to deliver light to a patient area adjacent to the treatment head. The apparatus includes a first articulated arm pivotably connected to the first treatment head at a first end and a second articulated arm pivotably connected to the second treatment head at a first end. The apparatus includes a handle. A first end of the handle is coupled to the first articulated arm at a second end of the first articulated arm distal to the first end of the first articulated arm. A second end of the handle, distal to the first end of the handle, is coupled to the second articulated arm at a second end of the second articulated arm distal to the first end of the second articulated arm.

19 Claims, 5 Drawing Sheets

(56) References Cited

U.S. PATENT DOCUMENTS

| | | | |
|---|---|---|---|
| 2012/0083772 A1 | 4/2012 | Rubinfeld et al. | |
| 2012/0140974 A1* | 6/2012 | Danielson | H04R 1/1066 |
| | | | 381/379 |
| 2013/0103017 A1* | 4/2013 | Weckwerth | A61B 18/203 |
| | | | 606/9 |
| 2014/0121731 A1 | 5/2014 | Brawn | |
| 2014/0316492 A1 | 10/2014 | Min et al. | |
| 2015/0209597 A1* | 7/2015 | Haarlander | A61H 23/02 |
| | | | 601/46 |
| 2015/0375007 A1* | 12/2015 | Takeuchi | A61N 5/0617 |
| | | | 607/90 |
| 2016/0158572 A1* | 6/2016 | Nolan | A61N 5/0603 |
| | | | 607/88 |
| 2017/0224951 A1* | 8/2017 | Weber | A61M 21/02 |
| 2017/0290731 A1 | 10/2017 | Eckhouse et al. | |
| 2017/0333728 A1* | 11/2017 | Sentis | A61N 5/0603 |
| 2018/0147416 A1* | 5/2018 | Segel | A61N 5/0619 |

FOREIGN PATENT DOCUMENTS

| | | |
|---|---|---|
| WO | 2012098548 A1 | 7/2012 |
| WO | 2017180663 A1 | 10/2017 |

* cited by examiner

PAIN TREATMENT DEVICE

FIELD

This invention relates to pain treatment devices and more particularly relates to a light emitting pain treatment device.

BACKGROUND

Light is used in pain treatment devices to heal wounds and reduce pain of a patient. Currently, light emitting pain treatment devices are typically a single treatment head attached to a stand or other stationary device, which is inconvenient. Some devices are handheld, but are single heads, which only covers a small area.

SUMMARY

An apparatus for pain treatment includes a first treatment head and a second treatment head, where each treatment head includes one or more light sources with different wavelengths oriented to deliver light from the one or more sources to a patient area adjacent to the treatment head. The apparatus includes a first articulated arm pivotably connected to the first treatment head at a first end of the first articulated arm and a second articulated arm pivotably connected to the second treatment head at a first end of the second articulated arm. The apparatus includes a handle. A first end of the handle is coupled to the first articulated arm at a second end of the first articulated arm distal to the first end of the first articulated arm. A second end of the handle, distal to the first end of the handle, is coupled to the second articulated arm at a second end of the second articulated arm distal to the first end of the second articulated arm.

Another apparatus for pain treatment includes a first treatment head and a second treatment head. Each treatment head includes a first light source emitting light at a first wavelength, a second light source emitting light at second wavelength, and a third light source emitting light at a third light source, where the light sources are each oriented to deliver light to an area on a patient in contact with the treatment head. The apparatus includes a first articulated arm pivotably connected to the first treatment head at a first end of the first articulated arm and a second articulated arm pivotably connected to the second treatment head at a first end of the second articulated arm. The apparatus includes a handle. A first end of the handle is coupled to the first articulated arm at a second end of the first articulated arm distal to the first end of the first articulated arm, and a second end of the handle, distal to the first end of the handle, is coupled to the second articulated arm at a second end of the second articulated arm distal to the first end of the second articulated arm. The first articulated arm and the second articulated arm extend away from the handle in a same direction toward the patient.

Another apparatus for pain treatment includes a first treatment head and a second treatment head. Each treatment head includes a first light source emitting light at a first wavelength, a second light source emitting light at second wavelength, and a third light source emitting light at a third light source, where the light sources are each oriented to deliver light to an area on a patient in contact with the treatment head. The apparatus includes a first articulated arm pivotably connected to the first treatment head at a first end of the first articulated arm and a second articulated arm pivotably connected to the second treatment head at a first end of the second articulated arm. The apparatus includes a handle. A first end of the handle is coupled to the first articulated arm at a second end of the first articulated arm distal to the first end of the first articulated arm, and a second end of the handle, distal to the first end of the handle, is coupled to the second articulated arm at a second end of the second articulated arm distal to the first end of the second articulated arm. The first articulated arm and the second articulated arm extend away from the handle in a same direction toward the patient.

In the embodiment, the apparatus includes a control module disposed within the handle, first articulated arm and/or second articulated arm and a user interface that controls treatment parameters of the first and second treatment heads, wherein the user plurality of treatment modes where each treatment mode includes a unique combination of intensity and/or duty cycle of each of the first, second and third light sources. The first articulated arm and/or the second articulated arm is adjustably connected to the handle and movement of the first articulated arm, the second articulated arm or both the first articulated arm and the second articulated arm adjust a width between the first treatment head and the second treatment head. The pivotal connection between the first treatment head and the first articulated arm and the pivotal connection between the second treatment head and the second articulated arm each include a hinge configured to allow movement of the first treatment head and the second treatment head in a direction through a plane running through the handle, the first articulated arm and the second articulated arm, and the pivotal connection between the first treatment head and the first articulated arm and the pivotal connection between the second treatment head and the second articulated arm are configured so a light emission side of the first treatment head and a light emission side of the second treatment head are positionable in a range from facing each other to facing a same direction.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system."

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture ("ISA") instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider). In some embodiments, electronic circuitry including, for example, programmable logic circuitry, field-programmable gate arrays ("FPGA"), or programmable logic arrays ("PLA") may execute the computer readable program instructions by utilizing state information of the computer readable program instructions to personalize the electronic circuitry, in order to perform aspects of the present invention.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program instructions may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of" includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C." As used herein, "a member selected from the group consisting of A, B, and C and combinations thereof" includes only A, only B, only C, a combination of A and B, a combination of B and C, a combination of A and C or a combination of A, B and C.

An apparatus for pain treatment includes a first treatment head and a second treatment head, where each treatment head includes one or more light sources with different wavelengths oriented to deliver light from the one or more light sources to a patient area adjacent to the treatment head. The apparatus includes a first articulated arm pivotably connected to the first treatment head at a first end of the first articulated arm and a second articulated arm pivotably connected to the second treatment head at a first end of the second articulated arm. The apparatus includes a handle. A first end of the handle is coupled to the first articulated arm at a second end of the first articulated arm distal to the first end of the first articulated arm. A second end of the handle, distal to the first end of the handle, is coupled to the second articulated arm at a second end of the second articulated arm distal to the first end of the second articulated arm.

In some embodiments, the first articulated arm and the second articulated arm extend away from the handle in a same general direction. In other embodiments, the first articulated arm and/or the second articulated arm are adjustably connected to the handle where movement of the first articulated arm, the second articulated arm or both the first articulated arm and the second articulated arm adjust a width between the first treatment head and the second treatment head. In other embodiments, in response to a user setting a distance between the first treatment head and the second treatment head, the adjustable connection between the first articulated arm and/or the second articulated arm maintains a distance between the first treatment head and the second treatment head. In further embodiments, the adjustable connection between the first articulated arm and the handle and/or the second articulated arm and the handle maintains a position set by a user by resistance. In other embodiments, the adjustable connection between the first articulated arm and the handle and/or the second articulated arm and the handle maintains a position set by a user with a locking mechanism.

In some embodiments, the pivotal connection between the first treatment head and the first articulated arm and the pivotal connection between the second treatment head and the second articulated arm each include a hinge configured to allow movement of the first treatment head and the second treatment head in a direction through a plane running through the handle, the first articulated arm and the second articulated arm. In other embodiments, the pivotal connection between the first treatment head and the first articulated arm and the pivotal connection between the second treatment head and the second articulated arm each allow movement in a plurality of directions. In other embodiments, the pivotal connection between the first treatment head and the first articulated arm and the pivotal connection between the second treatment head and the second articulated arm are configured so a light emission side of the first treatment head and a light emission side of the second treatment head are positionable in a range from facing each other to facing a same direction.

In some embodiments, the handle is shaped to be wider than a hand of a user to allow gripping of the handle by the user while the first end and the second end of the handle extend beyond the hand and the first articulated arm and the second articulated arm extend away from the handle in the same general direction beyond where the user grips the handle. In other embodiments, the apparatus includes an audible alert where the audible alert emits a sound while the first and second treatment heads emit light and/or in response to turning on and off of light from the treatment heads. In other embodiments, the apparatus includes a control module that includes a mode adjustment that adjusts which of the plurality of light sources of a particular wavelength are turned on, intensity of each of the plurality of light sources, a duty cycle of each of the plurality of light sources and a duration of operation of the plurality of light sources. In other embodiments, the handle includes a self-contained power source and/or a user interface that controls treatment parameters of the first and second treatment heads.

Another apparatus for pain treatment includes a first treatment head and a second treatment head. Each treatment head includes a first light source emitting light at a first wavelength, a second light source emitting light at second wavelength, and a third light source emitting light at a third light source, where the light sources are each oriented to deliver light to an area on a patient in contact with the treatment head. The apparatus includes a first articulated arm pivotably connected to the first treatment head at a first end of the first articulated arm and a second articulated arm pivotably connected to the second treatment head at a first end of the second articulated arm. The apparatus includes a handle. A first end of the handle is coupled to the first articulated arm at a second end of the first articulated arm distal to the first end of the first articulated arm, and a second end of the handle, distal to the first end of the handle, is coupled to the second articulated arm at a second end of the second articulated arm distal to the first end of the second articulated arm. The first articulated arm and the second articulated arm extend away from the handle in a same direction toward the patient.

In some embodiments, the apparatus includes a control module disposed within the handle where the control module controls selection between a plurality of treatment modes. Each treatment mode includes a unique combination of intensity and/or duty cycle of each of the first, second and third light sources. In other embodiments, the first articulated arm and/or the second articulated arm is adjustably connected to the handle and movement of the first articulated arm, the second articulated arm or both the first articulated arm and the second articulated arm adjust a width between the first treatment head and the second treatment head. In other embodiments, the adjustable connection between the first articulated arm and the handle and/or the second articulated arm and the handle maintains a position set by a user. In other embodiments, the pivotal connection between the first treatment head and the first articulated arm and the pivotal connection between the second treatment head and the second articulated arm each include a hinge configured to allow movement of the first treatment head and the second treatment head in a direction through a plane running through the handle, the first articulated arm and the second articulated arm.

Another apparatus for pain treatment includes a first treatment head and a second treatment head. Each treatment head includes a first light source emitting light at a first wavelength, a second light source emitting light at second wavelength, and a third light source emitting light at a third light source, where the light sources are each oriented to deliver light to an area on a patient in contact with the treatment head. The apparatus includes a first articulated arm pivotably connected to the first treatment head at a first end of the first articulated arm and a second articulated arm pivotably connected to the second treatment head at a first end of the second articulated arm. The apparatus includes a handle. A first end of the handle is coupled to the first articulated arm at a second end of the first articulated arm distal to the first end of the first articulated arm, and a second end of the handle, distal to the first end of the handle, is coupled to the second articulated arm at a second end of the second articulated arm distal to the first end of the second articulated arm. The first articulated arm and the second articulated arm extend away from the handle in a same direction toward the patient.

In the embodiment, the apparatus includes a control module disposed within the handle, first articulated arm and/or second articulated arm and a user interface that controls treatment parameters of the first and second treatment heads, wherein the user interface includes a mode selector that directs the control module to select between a plurality of treatment modes where each treatment mode includes a unique combination of intensity and/or duty cycle of each of the first, second and third light sources. The first articulated arm and/or the second articulated arm is adjustably connected to the handle and movement of the first articulated arm, the second articulated arm or both the first articulated arm and the second articulated arm adjust a width between the first treatment head and the second treatment head.

The pivotal connection between the first treatment head and the first articulated arm and the pivotal connection between the second treatment head and the second articulated arm each include a hinge configured to allow movement of the first treatment head and the second treatment head in a direction through a plane running through the handle, the first articulated arm and the second articulated arm, and the pivotal connection between the first treatment head and the first articulated arm and the pivotal connection between the second treatment head and the second articulated arm are configured so a light emission side of the first treatment head and a light emission side of the second treatment head are positionable in a range from facing each other to facing a same direction. In some embodiments, the apparatus includes a self-contained power source.

Figure 1A:
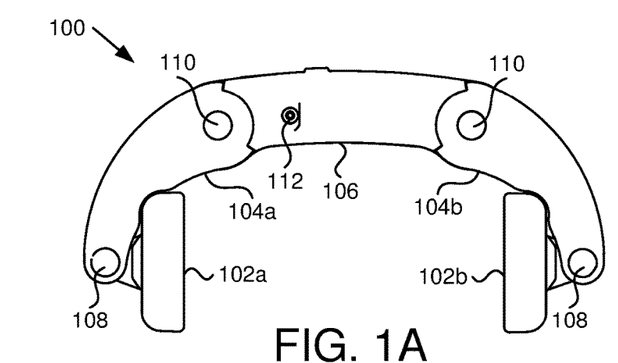
FIG. 1A is a front view illustrating one embodiment of a pain treatment device with treatment heads facing each other.
Figure 1B:
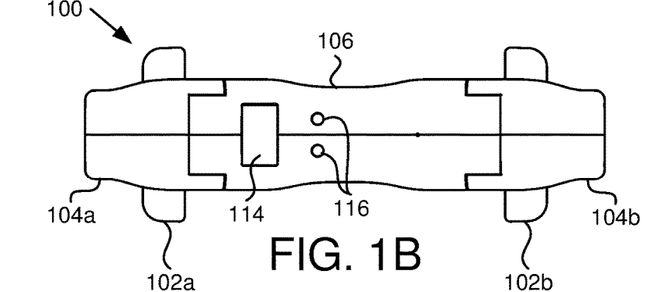
FIG. 1B is a top view further illustrating the pain treatment device of FIG. 1A.
Figures 1C, 1D:
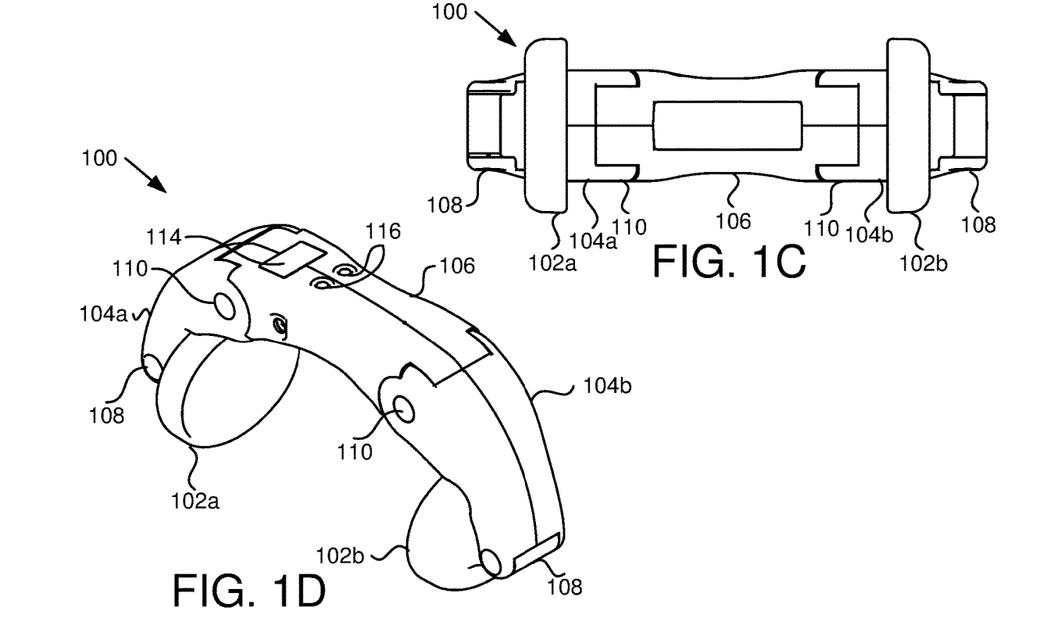
FIG. 1C is a bottom view further illustrating the pain treatment device of FIG. 1A.
FIG. 1D is a perspective view further illustrating the pain treatment device of FIG. 1A.
Figure 1E:
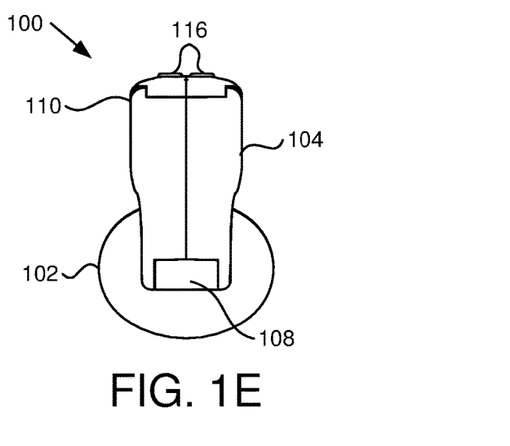
FIG. 1E is a side view further illustrating the pain treatment device of FIG. 1A.
Figure 2A:
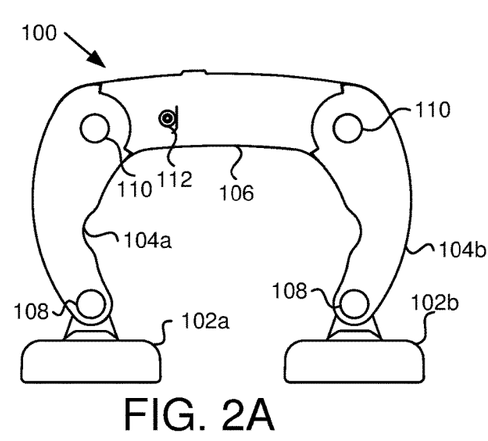
FIG. 2A is a front view illustrating one embodiment of a pain treatment device with treatment heads facing down.
Figure 2B:
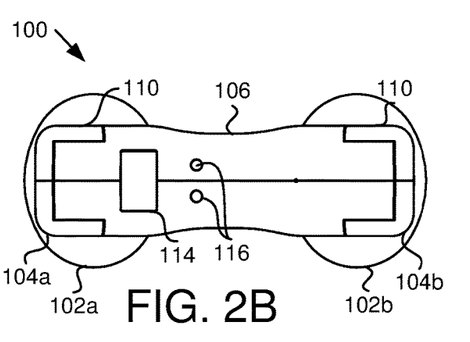
FIG. 2B is a top view further illustrating the pain treatment device of FIG. 2A.
Figure 2C:
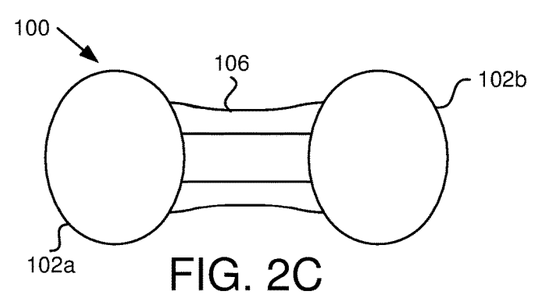
FIG. 2C is a bottom view further illustrating the pain treatment device of FIG. 2A.
Figure 2D:
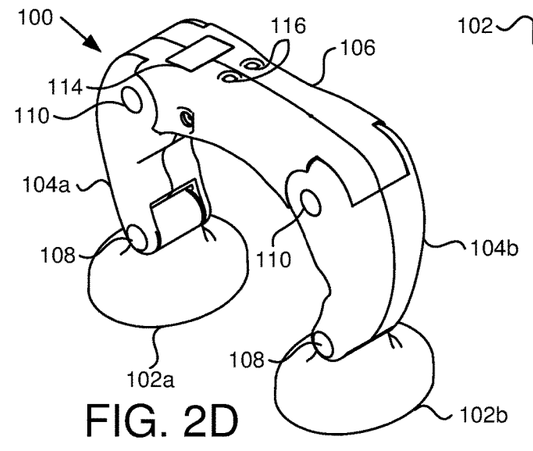
FIG. 2D is a perspective view further illustrating the pain treatment device of FIG. 2A.
Figure 2E:
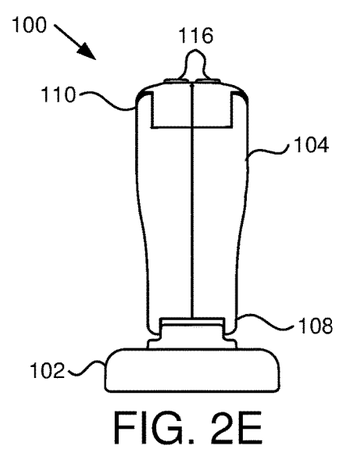
FIG. 2E is a side view further illustrating the pain treatment device of FIG. 2A.

FIG. 1A is a front view illustrating one embodiment of a pain treatment device 100 with treatment heads 102 facing each other. FIG. 1B is a top view, FIG. 1C is a bottom view, FIG. 1D is a perspective view, and FIG. 1E is a side view further illustrating the pain treatment device 100 of FIG. 1A. FIG. 2A is a front view illustrating one embodiment of the pain treatment device 100 with treatment heads 102 facing down. FIG. 2B is a top view, FIG. 2C is a bottom view, FIG. 2D is a perspective view, and FIG. 2E is a side view further illustrating the pain treatment device 100 of FIG. 2A. The pain treatment device 100 includes a first treatment head 102a and a second treatment head 102b (e.g. "treatment heads 102" or generically "treatment head 102"). The treatment heads 102 include one or more light sources. Where the treatment heads 102 include more than one light source, each has a different wavelength and is oriented to deliver light from the light sources to a patient area adjacent to the treatment heads 102.

The patient area is an area of skin on a patient that is being treated. The treatment heads 102 deliver light to the patient treatment area by being in contact with the patient treatment area or by being placed close to the patient treatment area so that the treatment heads 102 are pointed at the patient treatment area. Note that because there are two treatment heads 102a, 102b, the patient treatment area may include two areas that are separate. In other embodiments, the two treatment heads 102a, 102b are pointed at a single patient treatment area that is large enough so that both treatment heads 102a, 102b affect the patient treatment area. The patient treatment area may also be located below the skin of the patient, such as a muscle, tissue, a joint, etc. The pain treatment device 100 is not limited to treatment of pain, but may also be used for treatment of a wound, treatment of an injury, or any other symptom or condition of a body where light therapy is useful.

The treatment heads 102 include a plurality of light sources where the light sources each emit light at a particular wavelength so that there are at least two different kinds of light sources, each emitting a separate wavelength. For example, a treatment head 102 may include three types of light sources where each type emits light at a different wavelength. The treatment heads 102, in some embodiments, include multiple light sources of a particular type. In other words, in some embodiments a treatment head 102 has three different types of light sources and the treatment head includes one or more light sources of each type. For example, a treatment head 102 may include several light sources of a first wavelength, several light sources of a second wavelength and several light sources of a third wavelength.

The wavelengths may be selected to treat different conditions. In one embodiment, the light sources emitting the first wavelength is a visible source of 670 nanometers ("nm"), the light sources emitting the second wavelength is a laser light source of 808 nm, and the light sources emitting the third wavelength is a laser light source of 905 nm. The visible light sources are often associated with pain relief and healing at the skin surface. The 808 nm light sources are intended for treatment of muscle and tissue under the skin and the 905 nm light sources are intended for treatment of joints and other deep tissue. The pain treatment device 100 may include any number of light sources that emit light at any number of wavelengths. One of skill in the art will recognize other appropriate wavelengths to be included and a number of light sources of each wavelength to include.

The first treatment head 102a is connected to a first end of a first articulated arm 104a and the second treatment head 102b is connected to a first end of a second articulated arm 104b. The pain treatment device 100 includes a handle 106 where a first end of the handle 106 is coupled to the first articulated arm 104a at a second end of the first articulated arm 104a distal to the first end of the first articulated arm 104a, and a second end of the handle 106, distal to the first end of the handle 106, is coupled to the second articulated arm 104b at a second end of the second articulated arm 104b distal to the first end of the second articulated arm 104b, as depicted in FIGS. 1A, 1B, 1D, 2A, 2B and 2D.

In one embodiment, the treatment heads 102 are pivotably connected to the articulated arms 104. As used herein, a treatment head 102 pivotably connected to an articulated arm 104 includes a connection where the treatment head 102 can move in one or more directions with respect to the attached articulated arm 104. In some embodiments, each treatment head 102 is pivotably connected to a corresponding articulated arm 104 with a hinge 108 configured to allow movement of the first treatment head 102a and the second treatment head 102b in a direction through a plane running through the handle 106, the first articulated arm 104a and the second articulated arm 104b. For example, the first treatment head 102a and the second treatment head 102b are allowed to move from the position shown in FIGS. 1A-E to the position shown in FIGS. 2A-E.

Figure 3:
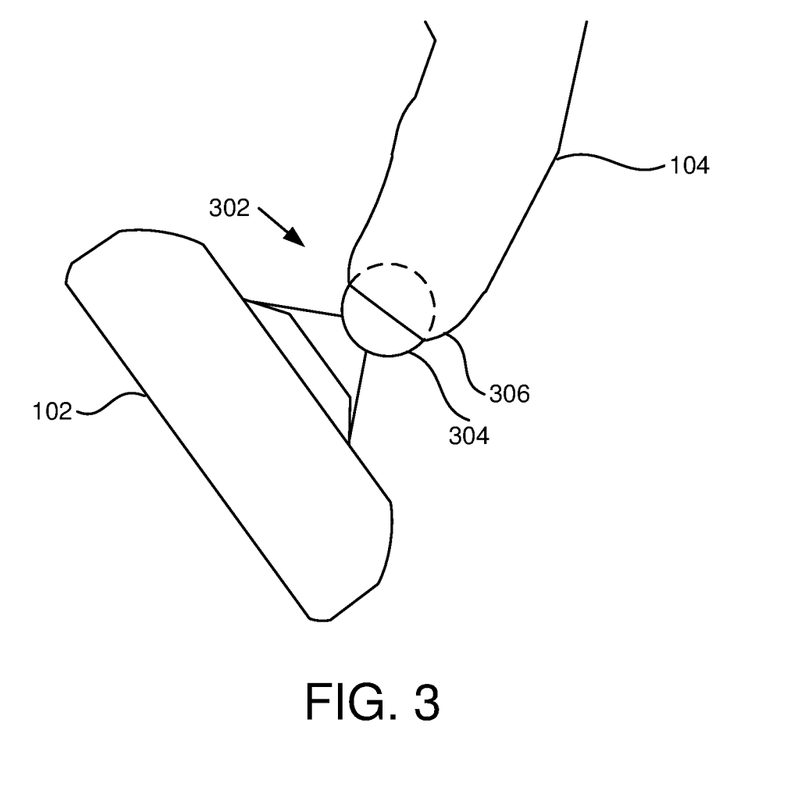
FIG. 3 is a detailed view of a treatment head connected to an articulated arm with a ball joint.

In some embodiments the pivotal connection between a treatment head 102 and an articulated arm 104 each allow movement in a plurality of directions. For example, the pivotal connection may include a ball joint 302, as depicted in FIG. 3 where the treatment head 102 is attached to a spherical structure 304 that fits in a joint 306 of the articulated arm 104, or vice versa. One of skill in the art will recognize other pivotal connections that allow movement in a plurality of directions.

In some embodiments, the pivotal connection between the first treatment head 102a and the first articulated arm 104a and the pivotal connection between the second treatment head 102b and the second articulated arm 104b are configured so a light emission side of the first treatment head 102a and a light emission side of the second treatment head 102b are positionable in a range from facing each other to facing a same direction. As used herein, the light emission side of the first treatment head 102a and the light emission side of the second treatment head 102b positionable in a range from facing each other to facing a same direction includes having the light emission sides parallel to each other or nearly parallel to each other, for example within five degrees of parallel, but not exactly parallel. In one example, the articulating arms 104 are curved to accommodate the treatment heads 102 facing each other. In addition, the light emission side of the first treatment head 102a and the light emission side of the second treatment head 102b positionable facing a same direction also includes a range that may be nearly facing the same direction, such as within five degrees of facing a same direction.

In other embodiments, the pivotal connection between the first treatment head 102a and the first articulated arm 104a and the pivotal connection between the second treatment head 102b and the second articulated arm 104b are configured so a light emission side of the first treatment head 102a and a light emission side of the second treatment head 102b are positionable to face away from the handle 106, as depicted in FIGS. 2A-E. In other embodiments, the treatment heads 102 may pivot past the position shown in Figures to face partially or fully outward away from a center between the treatment heads 102 (not shown).

In some embodiments, the articulated arms 104 include another joint (not shown) between the first end and the second end of the articulated arms 104 to enable additional positioning of the treatment heads 102 at various angles or to be positioned to face each other. One of skill in the art will recognize other configurations of the articulated arms 104 and treatment heads 102 to allow additional positions of the treatment heads 102 with respect to patient treatment areas.

In some embodiments, the first articulated arm 104a and the second articulated arm 104b extend away from the handle 106 in a same general direction. For example, the first articulated arm 104a and the second articulated arm 104b extend away from the handle 106 so that a centerline of the handle 106, a centerline of the first articulated arm 104a and a centerline of the second articulated arm 104b are in a common plane, as depicted in FIGS. 1A-E and 2A-E. In some embodiments, a centerline of the treatment heads 102 also runs along the plane.

In some embodiments, the first articulated arm 104a and/or the second articulated arm 104b are adjustably connected to the handle 106 where movement of the first articulated arm 104a, the second articulated arm 104b or both the first articulated arm 104a and the second articulated arm 104b adjust a width between the first treatment head 102a and the second treatment head 102b. Adjustment of the width between the treatment heads 102 allows a user to accommodate various body parts of different widths.

In some embodiments, in response to a user setting a distance between the first treatment head 102a and the second treatment head 102b, the adjustable connection 110 between the first articulated arm 104a and/or the second articulated arm 104b maintains a distance between the first treatment head 102a and the second treatment head 102b. In one example, the adjustable connection between the first articulated arm 104a and the handle 106 and/or the second articulated arm 104b and the handle 106 maintains a position set by a user by resistance. For example, the adjustable connection 110 between an articulated arm 104 and the handle 106 is constructed to allow movement of an articulated arm 104 with respect to the handle 106 and once a user stops moving the articulated arm 104, the articulated arm 104 maintains the position of the articulated arm 104 with respect to the handle 106 while a treatment head 102 connected to the handle 106 is used on a patient and movement of the articulated arm 104 with respect to the handle 106 requires force above a threshold where the threshold is set to prevent movement in the adjustable connection 110 when the treatment heads 102 are being used to treat a patient.

In other embodiments, the adjustable connection 110 between the first articulated arm 104a and the handle 106 and/or the second articulated arm 104b and the handle 106 maintains a position set by a user with a locking mechanism. For example, the locking mechanism may include a lever that locks an articulated arm 104 in place with respect to the handle 106. The lever tightens the adjustable connection 110 to prevent movement. In another embodiment, the locking mechanism is a knob, nut, etc. that can be screwed to tighten the adjustable connection 110. One of skill in the art will recognize other ways to allow movement of the articulated arms 104 with respect to the handle 106 and then prevent unwanted movement once a position of the articulated arms 104 is set with respect to the handle 106.

In some embodiments, the handle 106 is shaped to be wider than a hand of a user to allow gripping of the handle 106 by the user while the first end and the second end of the handle 106 extend beyond the hand and the first articulated arm 104a and the second articulated arm 104a extend away from the handle 106 in the same general direction beyond where the user grips the handle 106. In the embodiment, the handle 106 is size and configured to allow a user to wrap the user's fingers of the user's hand around the handle 106 and grip the handle 106. In the embodiment, the articulated arms 104 are long enough to extend the treatment heads 102 beyond the fingers and other parts of the user's hand. In other embodiments, the handle 106 is wide enough to accommodate one, two or three fingers around the handle 106. In other embodiments, the handle 106 includes an extension, knob, etc. (not shown) above where the handle 106 intersects with the articulated arms 104. One of skill in the art will recognize other ways to configure the handle 106 to allow a user to hold the handle 106 while the treatment heads 102 are positioned to deliver light to a patient treatment area.

FIG. 2C depicts the treatment heads 102 as having an oval shape. In other embodiments, the treatment heads 102 are circular. In other embodiments, the treatment heads 102 are square, rectangular or another shape. FIGS. 1A-C, 2A and 2E depict the treatment heads 102 having a flat bottom, which is a light emission side. In other embodiments, the light emission side of the treatment heads 102 is concave, convex, or other shape. The light emission side of the treatment heads 102, in some embodiments, is configured to be placed against the skin of a patient and is rigid enough to maintain a same shape when touching a patient. In other embodiments, the light emission side of the treatment heads 102 is configured to have some flex when pressed against the skin of the patient.

In some embodiments, the light emission side of the treatment heads 102 is plastic, glass, etc. without any type of lens to change direction of light. In other embodiments, the light emission side of the treatment heads 102 is a Fresnel lens or other lens to direct light in a particular direction, pattern, etc. In one embodiment, the light emission side of the treatment heads 102 are transparent. In other embodiments, the light emission side of the treatment heads 102 are colored (such as red), but are transparent or translucent. One of skill in the art will recognize other configurations of the light emission side of the treatment heads 102 and will recognize suitable materials.

Figure 4:
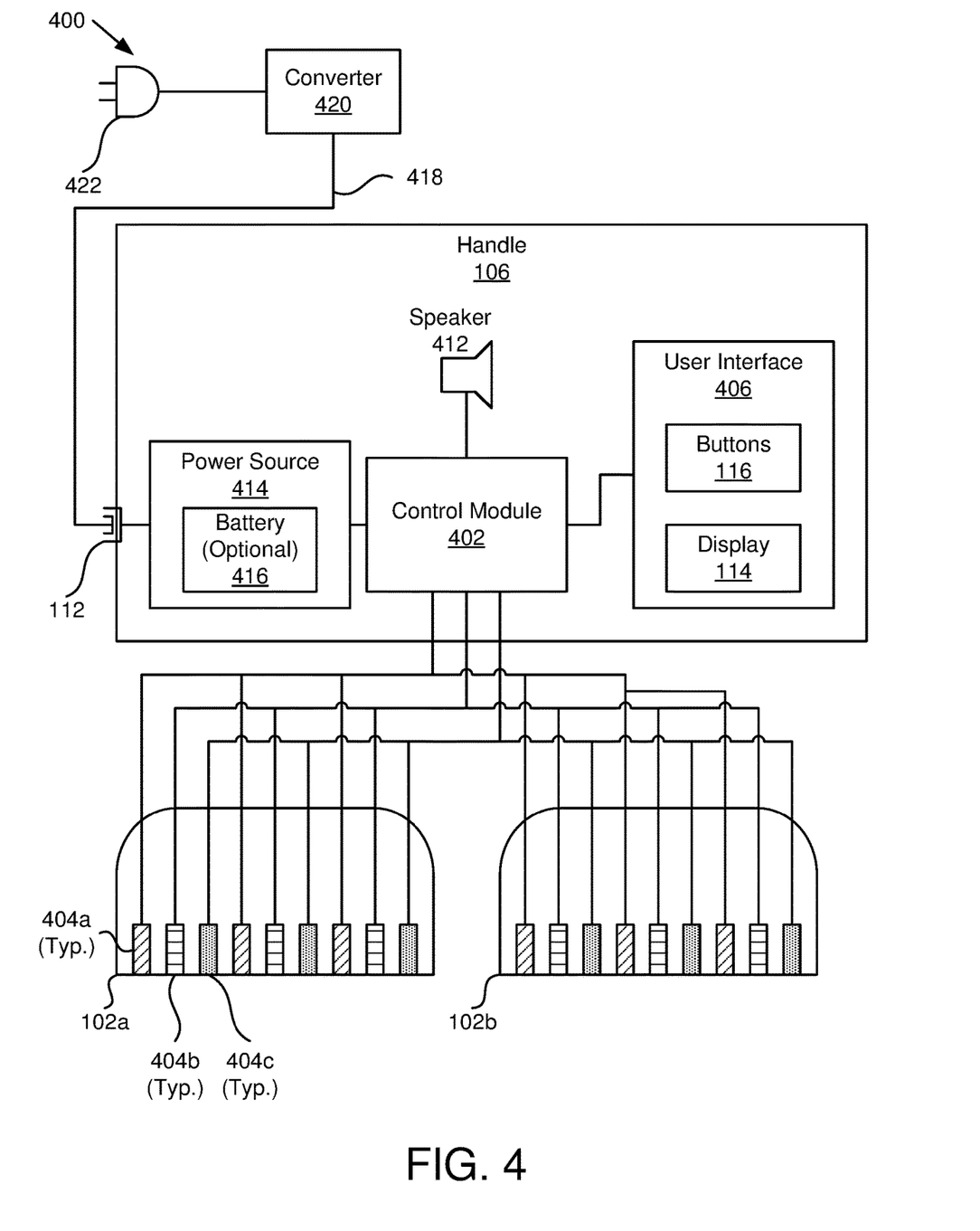
FIG. 4 is a schematic block diagram of a control system for a pain treatment device.

FIG. 4 is a schematic block diagram of a control system 400 for a pain treatment device 100. The control system 400 includes a control module 402 connected to light sources 404 in the treatment heads 102, a user interface 406 with buttons 116 and a display 114, a speaker 412, a power source 414 with an optional battery 416, a power connection 112, a power cord 418, a converter 420 and a plug 422, which are described below.

The control system 400 includes a control module 402 that controls light emission from the treatment heads 102. The treatment heads 102, as depicted in FIG. 4, include multiple light sources 404. In some embodiments, the treatment heads 102 include three different types of light sources 404 where each type of light source (e.g. 404a, 404b, 404c) emits light of a different wavelength. For example, a first type of light source 404a may emit infrared or visible light, a second type of light source 404b may emit laser light of a first wavelength and a third type of light source 404c may emit a laser light of a second wavelength where each type of light source 404a, 404b, 404c serves a different purpose.

Each treatment head 102 is depicted with two light sources of each type 404a, 404b, 404c for convenience. One of skill in the art will recognize how to arrange one or more light sources of each type 404a, 404b, 404c in various patterns to deliver light from each type of light source 404a, 404b, 404c in a particular pattern, intensity, etc.

In some embodiments, the control module includes a mode adjustment that adjusts various aspects of the light sources, such as which of the plurality of light sources 404a, 404b, 404c of a particular wavelength are turned on, intensity of each of the plurality of light sources 404a, 404b, 404c, a duty cycle of each of the plurality of light sources 404a, 404b, 404c, a duration of operation of the plurality of light sources 404a, 404b, 404c, and the like.

In some embodiments, the mode adjustment has three settings: skin mode, muscle mode and joint mode. In other embodiments, the mode adjustment includes other modes or combinations thereof. In one embodiment, the first type of light source 404a is a visible source that emits light at a wavelength of 670 nm (red light) and there are five light sources 404a, each with a peak output of about 300 milliwatts ("mW"). In some embodiments, the visible light sources 404a are pulsed at 100 microseconds ("0") for a duty cycle of 10 percent.

In some embodiments, the second type of light source 404b is a laser light source that emits light at a wavelength of 808 nm and are infrared ("IR") diode lasers. In some embodiments, there are six light sources 404b of this second type, each with a peak output of about 300 mW, which may be pulsed at 100 μS for a duty cycle of 2 percent. In some embodiments, the third type of light source 404c is a laser light source that emits light at a wavelength of 905 nm and are IR diode lasers. In some embodiments, there are four light sources 404c of this third type, each with a peak output of about 15,000 mW, which may be pulsed at 100 nanoseconds ("nS") for a duty cycle of 0.033 percent.

In some embodiments, in skin mode the first type of light source 404a is on constantly, the second type of light source 404b is on for 0.5 seconds per second, and the third type of light source 404c is on for 0.33 seconds per second. In some embodiments, in muscle mode the first type of light source 404a is on for 0.5 seconds per second, the second type of light source 404b is on constantly, and the third type of light source 404c is on for 0.5 seconds per second. In some embodiments, in joint mode the first type of light source 404a is on for 0.33 seconds per second, the second type of light source 404b is on for 0.5 seconds per second, and the third type of light source 404c is on constantly. One of skill in the art will recognize other intensities and durations for various modes.

When the one type of light source (e.g. 404a) is in the visible range (e.g. red light), the light source 404a may be used as a visual indicator that light is being emitted from the treatment heads 102. In other embodiments, the control module 402 controls the speaker 412 to emit a sound to indicate operation of the light sources 404, a particular mode, etc. In one example, the control module 402 causes the speaker 412 to emit a tone when the treatment heads 102 are turned on or off. In another example, the control module 402 causes the speaker 412 to emit a tone when the treatment heads 102 are operational, such as a tone every 5 seconds, every 10 seconds, etc. so a user/patient knows when that the treatment heads 102 are emitting light when the patient area is not visible to the patient (e.g. on the patient's back). In other embodiments, the control module 402 causes the speaker 412 to play a sound, a phrase, provide instructions, etc.

The control module 402 includes a user interface 406 to allow a user to set a mode, turn the treatment heads 102 on or off, to set light intensity, to notify a user, etc. For example, the user interface 406 may include one or more buttons 116 to allow a user to change settings, set a timer, choose a mode, etc. In other embodiments, the user interface 406 includes a display 114, which conveys information to the user, such as on or off, which mode is selected, a battery level, a time before shutoff, etc. In other embodiments, the display 114 is a touchscreen. Where the display 114 is a touchscreen, the buttons 116 may be on the touchscreen. In some embodiments, the control module 402 includes a timer and the user interface 406 allows a user to set a time on the timer before the control module 402 shuts off the treatment heads 102. For example, the timer may have 1, 3 and 5 minute options.

The control module 402 and other components are powered by a power source 414. The power source 414, in some embodiments, directs power from a battery 416 or from a converter 420 to the control module 402. In some embodiments, the power source 414 includes one or more converters that convert an alternating current ("AC") voltage and/or direct current ("DC") voltage to one or more DC voltages. For example, the power source 414 may control charge and discharge of the battery 416. In some embodiments, the power source 414 does not include a battery 416 and the pain treatment device 100 is powered from an external source. The external source may be utility power from a plug 422 or may be DC power from a converter 420, which is powered through the plug 422 where the plug 422 is configured to be inserted in a wall outlet or other power source.

In some embodiments, the power source 414 is low voltage, such as 18 volts. For example, the converter 420 provides a low voltage for safety. In some embodiments, the handle 106 includes a power connection 112, which includes a jack which allows a power cord 418 from the converter 420 to be plugged into the jack. The power cord 418 may be removed once the battery 416 is charged for ease of operation of the pain treatment device 100.

Figure 5:
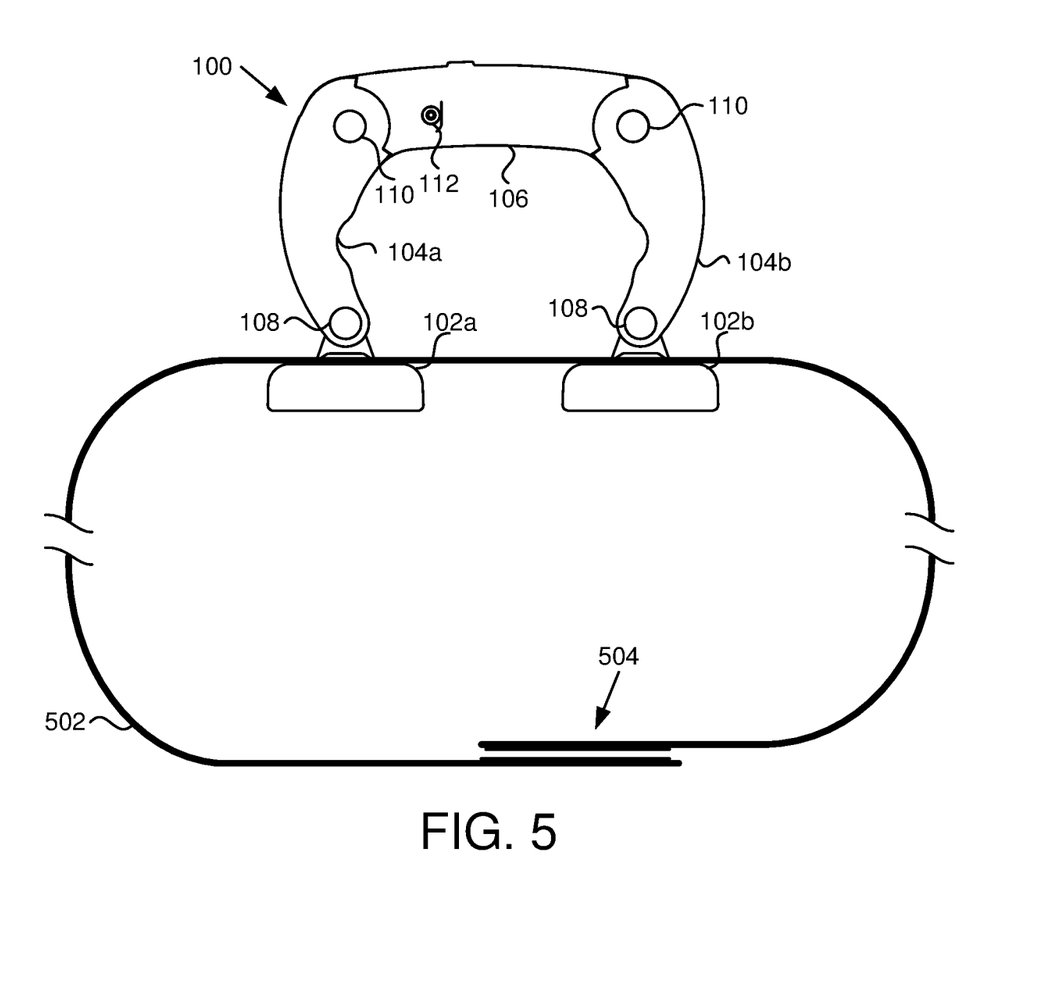
FIG. 5 is a front view illustrating one embodiment of a pain treatment device with treatment heads facing down and a strap.

FIG. 5 is a front view illustrating one embodiment of a pain treatment device 100 with treatment heads 102 facing down and a strap 502. The strap 502 connects to the pain treatment device 100 and enables maintaining the pain treatment device 100 on a patient without another user or the patient holding the pain treatment device 100. The strap 502 may be of various lengths and may include a hook and loop fastener 504 or other fastening device, such as a buckle to hold the strap 502 in place. In some embodiments, the strap 502 has an adjustable length.

In some embodiments, the strap 502 includes slots (not shown) to allow the treatment heads 102 to be placed in the slots. In one embodiment, a first slot is sized just long enough for the first treatment head 102a to be inserted in the slot while a second slot is longer to allow the second treatment head 102b to move closer and farther away from the first treatment head 102a for adjustment of a width between the treatment heads 102. In other embodiments, the strap 502 includes one or more attachments to other parts of the pain treatment device 100 for stability. In other embodiments, a width and rigidity of the strap 502 maintains the treatment heads 102 in position and accounts for lateral forces due to weight of the handle 106 and articulated arms 104.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treatment comprising:
   selecting a portion of a body of a patient being treated, the portion comprising any one or more of an area of skin, a muscle, and a joint;
   positioning a light treatment apparatus against the portion of the body of the patient being treated, the light treatment apparatus comprising:
   a first treatment head and a second treatment head, wherein each treatment head comprises one or more light sources with different wavelengths oriented to deliver light from the one or more light sources to a patient area adjacent to the treatment head;
   a first articulated arm pivotably connected to the first treatment head at a first end of the first articulated arm;
   a second articulated arm pivotably connected to the second treatment head at a first end of the second articulated arm; and
   a handle, wherein a first end of the handle comprises a first connection coupling the handle and the first articulated arm at a second end of the first articulated arm opposite the first end of the first articulated arm, wherein a second end of the handle, opposite the first end of the handle, comprises a second connection coupling the handle and the second articulated arm at a second end of the second articulated arm opposite the first end of the second articulated arm, wherein the first connection and the second connection are adjustable, and wherein the adjustable first connection and/or the adjustable second connection is configured to maintain a lateral distance between the first treatment head and the second treatment head in response to a position of the adjustable first connection and/or the adjustable second connection being set, wherein positioning the light treatment apparatus against the portion of the body of the patient being treated comprises:

rotating the first and second treatment heads to an angle to fit against the portion of the body being treated, the first and second heads positionable at least from against a same side of the portion of the body being treated in a direction away from the handle to against opposing sides of the portion of the body being treated; and adjusting a width between the first and second treatment heads to rest against the portion of the body being treated by adjusting the first and second articulated arms;

turning on one or more of the light sources of each of the first and second treatment heads; and turning off the one or more light sources of the first and second treatment heads after a period of time.

2. The method of treatment of claim 1, wherein the first articulated arm and the second articulated arm extend away from the handle in a same general direction.

3. The method of treatment of claim 1, wherein the adjustable first connection between the handle and the first articulated arm and/or the adjustable second connection between the handle and the second articulated arm are configured to adjust a width between the first treatment head and the second treatment head.

4. The method of treatment of claim 1, wherein the position of the adjustable first connection and/or the adjustable second connection is set by a user by resistance.

5. The method of treatment of claim 1, wherein the position of the adjustable first connection and/or the adjustable second connection is set by a user with a locking mechanism.

6. The method of treatment of claim 1, wherein the pivotal connection between the first treatment head and the first articulated arm and the pivotal connection between the second treatment head and the second articulated arm each comprise a hinge configured to allow movement of the first treatment head and the second treatment head in a direction through a plane running through the handle, the first articulated arm and the second articulated arm.

7. The method of treatment of claim 1, wherein the pivotal connection between the first treatment head and the first articulated arm and the pivotal connection between the second treatment head and the second articulated arm each allow movement in a plurality of directions.

8. The method of treatment of claim 1, wherein the handle is shaped to be wider than a hand of a user to allow gripping of the handle by the user while the first end and the second end of the handle extend beyond the hand and the first articulated arm and the second articulated arm extend away from the handle in the same general direction beyond where the user grips the handle.

9. The method of treatment of claim 1, further comprising an audible alert, wherein the audible alert emits a sound while the first and second treatment heads emit light and/or in response to turning on and off of light from the treatment heads.

10. The method of treatment of claim 1, further comprising selecting a light mode via a mode adjustment of a control module wherein the mode adjustment adjusts:

which of the plurality of light sources of a particular wavelength are turned on;

intensity of each of the plurality of light sources;

a duty cycle of each of the plurality of light sources; and a duration of operation of the plurality of light sources.

11. The method of treatment of claim 1, wherein the handle comprises:

a self-contained power source inside the handle; and a user interface that controls treatment parameters of the first and second treatment heads, wherein the user interface is integrated into a surface of the handle.

12. The method of treatment of claim 1, wherein:

when the portion of the body of the patient being treated is skin, positioning the light treatment against the portion of the body of the patient being treated comprises placing the first and second heads against the skin of the portion of the body of the patient being treated and further comprising selecting a skin mode comprising selecting one or more of the light sources that emit light of a wavelength for treatment of skin;

when the portion of the body of the patient being treated is muscle, positioning the light treatment against the portion of the body of the patient being treated comprises placing the first and second heads on or around the muscle of the portion of the body of the patient being treated and further comprising selecting a muscle mode comprising selecting one or more of the light sources that emit light of a wavelength for treatment of muscle; and when the portion of the body of the patient being treated is a joint, positioning the light treatment against the portion of the body of the patient being treated comprises placing the first and second heads on or around the joint of the portion of the body of the patient being treated and further comprising selecting a joint mode comprising selecting one or more of the light sources that emit light of a wavelength for treatment of a joint.

13. The method of treatment of claim 12, wherein the portion of the patient being treated is a first treatment area with a type comprising one of skin, muscle, and further comprising, in response to expiration of the period of time, repositioning the first and second treatment heads against a second treatment area of the body of the patient, the second treatment area comprising a type different than the first treatment area, selecting one of the skin mode, the muscle mode, and the joint mode applicable to the second treatment area, turning on one or more of the light sources of each of the first and second treatment heads according to the selected skin mode, muscle mode or joint mode, and turning off the one or more light sources of the first and second treatment heads after a second period of time.

14. The method of treatment of claim 1, further comprising securing a strap around a portion of the body of the patient, the strap configured to maintain the first and second treatment heads against the portion of the body of the patient being treated, the strap comprising a plurality of slots spaced along a length of the strap, each slot configured to accommodate one of the first treatment head and the second treatment head.

15. A method of treatment comprising:

selecting a portion of a body of a patient being treated, the portion comprising any one or more of an area of skin, a muscle, and a joint;

positioning a light treatment against the portion of the body of the patient being treated, the light treatment comprising:

a first treatment head and a second treatment head, wherein each treatment head comprises a first light source emitting light at a first wavelength, a second light source emitting light at second wavelength, and a third light source emitting light at a third wavelength, wherein the light sources are each oriented to deliver light to an area on a patient in contact with the treatment head;

a first articulated arm pivotably connected to the first treatment head at a first end of the first articulated arm via a pivotable first connection;

a second articulated arm pivotably connected to the second treatment head at a first end of the second articulated arm via a pivotable connection; and a handle, wherein a first end of the handle couples to the first articulated arm at a second end opposite the first end of the first articulated arm via a pivotable connection, wherein a second end of the handle, opposite the first end of the handle, couples to the second articulated arm at a second end opposite the first end of the second articulated arm via a pivotable connection, wherein the first articulated arm and the second articulated arm extend away from the handle in a same direction toward the patient, and wherein the pivotable connections of the second ends of the first and second articulated arms are configured to maintain a lateral distance between the first treatment head and the second treatment head in response to a position of the pivotable connection at the second ends of the first and second articulated arms being set, wherein the pivotal connection between the first treatment head and the first articulated arm and the pivotal connection between the second treatment head and the second articulated arm are configured so a light emission side of the first treatment head and a light emission side of the second treatment head are positionable in a range from facing each other to facing a same direction oriented away from the handle, wherein positioning the light treatment against the portion of the body of the patient being treated comprises:

rotating the first and second treatment heads to an angle to fit against the portion of the body being treated, the first and second heads positionable at least from against a same side of the portion of the body being treated in a direction away from the handle to against opposing sides of the portion of the body being treated; and adjusting a width between the first and second treatment heads to rest against the portion of the body being treated by adjusting the first and second articulated arms;

turning on the first light source, the second light source and/or the third light source of each of the first and second treatment heads; and turning off the first light source, the second light source, and/or the third light source of the first and second treatment heads after a period of time.

16. The method of treatment of claim 15, wherein turning on the first light source, the second light source, and/or the third light source further comprising selecting a light mode via a mode adjustment of a control module disposed within the handle, wherein the control module controls selection between a plurality of treatment modes, wherein each treatment mode comprises a unique combination of intensity and/or duty cycle of each of the first, second and third light sources.

17. The method of treatment of claim 15, wherein the pivotable connections at the second ends of the first and second articulated arms are configured to pivot respective positions of the first articulated arm and the second articulated arm with respect to the handle to adjust a width between the first treatment head and the second treatment head.

18. The method of treatment of claim 17, wherein the respective positions of the pivotable connections at the second ends of the first and second articulated arms are set by a user.

19. A method of treatment comprising:

selecting a portion of a body of a patient being treated, the portion comprising any one or more of an area of skin, a muscle, and a joint;

positioning a light treatment against the portion of the body of the patient being treated, the light treatment comprising:

a first treatment head and a second treatment head, wherein each treatment head comprises a first light source emitting light at a first wavelength, a second light source emitting light at second wavelength, and a third light source emitting light at a third wavelength, wherein the light sources are each oriented to deliver light to an area on a patient in contact with the treatment head;

a first articulated arm pivotably connected to the first treatment head at a first end of the first articulated arm via a pivotable first connection;

a second articulated arm pivotably connected to the second treatment head at a first end of the second articulated arm via a pivotable second connection;

a handle, wherein the pivotable first connection couples a first end of the handle to the first articulated arm at a second end of the first articulated arm opposite the first end of the first articulated arm, wherein the pivotable second connection couples a second end of the handle, opposite the first end of the handle to the second articulated arm at a second end of the second articulated arm opposite the first end of the second articulated arm, wherein the first articulated arm and the second articulated arm extend away from the handle in a same direction toward the patient, and wherein the pivotable first connection and/or the pivotable second connection are configured to maintain a lateral width between the first treatment head and the second treatment head in response to a position of the first pivotable connection and/or the second pivotable connection being set;

a control module disposed within the handle, first articulated arm and/or second articulated arm;

a self-contained power source inside the handle; and a graphical user interface that controls treatment parameters of the first and second treatment heads, wherein the user interface comprises a mode selector that directs the control module to select between a plurality of treatment modes, wherein each treatment mode comprises a unique combination of intensity and/or duty cycle of each of the first, second and third light sources, wherein the graphical user interface is integrated into a surface of the handle in a portion of the handle configured for the user to grasp the handle, wherein the apparatus is free from additional treatment heads other than the first treatment head and the second treatment head, and wherein the pivotal first connection between the first treatment head and the first articulated arm and the pivotal second connection between the second treatment head and the second articulated arm each comprise a hinge configured to allow movement of the first treatment head and the second treatment head in a direction through a plane running through the handle, the first articulated arm, and the second articulated arm, and the pivotal first connection between the first treatment head and the first articulated arm and the pivotal second connection between the second treatment head and the second articulated arm are configured so a first light emission side of the first treatment head and a second light emission side of the second treatment head are positionable in a range from facing each other to facing a same direction oriented away from the handle, wherein positioning the light treatment against the portion of the body of the patient being treated comprises:
  rotating the first and second treatment heads to an angle to fit against the portion of the body being treated, the first and second heads positionable at least from against a same side of the portion of the body being treated in a direction away from the handle to against opposing sides of the portion of the body being treated; and
  adjusting a width between the first and second treatment heads to rest against the portion of the body being treated by adjusting the first and second articulated arms;

turning on one or more of the light sources of each of the first and second treatment heads; and turning off the one or more light sources of the first and second treatment heads after a period of time.

* * * * *